United States Patent
Prior et al.

(10) Patent No.: US 10,980,571 B2
(45) Date of Patent: Apr. 20, 2021

(54) OCCLUSION DEVICES, SYSTEMS, AND METHODS

(71) Applicant: Covidien LP, Mansfield, MA (US)

(72) Inventors: Scott J. Prior, Shelton, CT (US); Danial P. Ferreira, Woodbridge, CT (US); Paul C. DiCesare, Shelton, CT (US); Walter S. Shunaula, West Haven, CT (US)

(73) Assignee: Covidien LP, Mansfield, MA (US)

( * ) Notice: Subject to any disclaimer, the term of this patent is extended or adjusted under 35 U.S.C. 154(b) by 289 days.

(21) Appl. No.: 15/973,658

(22) Filed: May 8, 2018

(65) Prior Publication Data

US 2019/0053828 A1 Feb. 21, 2019

Related U.S. Application Data

(60) Provisional application No. 62/545,703, filed on Aug. 15, 2017.

(51) Int. Cl.
*A61B 17/42* (2006.01)
*A61B 5/107* (2006.01)
(Continued)

(52) U.S. Cl.
CPC ........ *A61B 17/4241* (2013.01); *A61B 5/1076* (2013.01); *A61B 17/1204* (2013.01); *A61B 17/12099* (2013.01); *A61B 17/42* (2013.01); *A61B 17/12159* (2013.01); *A61B 17/3439* (2013.01); *A61B 2017/00557* (2013.01); *A61B 2017/00849* (2013.01); *A61B 2017/00862* (2013.01); *A61B 2017/345* (2013.01);
(Continued)

(58) Field of Classification Search
CPC .......... A61B 17/1204; A61B 17/12099; A61B 17/12159; A61B 17/3439; A61B 17/42; A61B 17/4241; A61B 17/12022; A61B 17/12027; A61B 17/12031; A61B 17/12036; A61B 2017/00557; A61B 2017/00849; A61B 2017/00862; A61B 2017/345; A61B 2017/4225; A61B 2090/037; A61M 13/003; A61M 2210/1433
See application file for complete search history.

(56) References Cited

U.S. PATENT DOCUMENTS 4,597,030 A 6/1986 Brody et al.
4,804,240 A 2/1989 Mori
(Continued)

FOREIGN PATENT DOCUMENTS

CN 202489982 U 10/2012
CN 202920313 U 5/2013
(Continued)

*Primary Examiner* — Jocelin C Tanner
(74) *Attorney, Agent, or Firm* — Carter, DeLuca & Farrell LLP

(57) ABSTRACT

An occlusion device includes a body having a plurality of layers and defining a first diameter. Each layer of the plurality of layers is releasably coupled to a respective inwardly-adjacent layer. An outermost layer of the plurality of layers is removable from the respective inwardly-adjacent layer. Removal of the outermost layer reduces an outer diameter of the body from the first diameter to a second diameter that is less than the first diameter.

20 Claims, 5 Drawing Sheets

(51) Int. Cl.
  *A61B 17/12* (2006.01)
  *A61M 13/00* (2006.01)
  *A61B 90/00* (2016.01)
  *A61B 17/00* (2006.01)
  *A61B 17/34* (2006.01)

(52) U.S. Cl.
  CPC .......... *A61B 2017/3429* (2013.01); *A61B 2017/4225* (2013.01); *A61B 2090/037* (2016.02); *A61M 13/003* (2013.01); *A61M 2210/1433* (2013.01)

(56) References Cited

U.S. PATENT DOCUMENTS

| | | | |
|---|---|---|---|
| 5,209,754 A * | 5/1993 | Ahluwalia | A61B 17/0218 600/207 |
| 5,394,863 A | 3/1995 | Sanford et al. | |
| 5,451,221 A | 9/1995 | Cho et al. | |
| 5,487,377 A | 1/1996 | Smith et al. | |
| 5,520,698 A | 5/1996 | Koh | |
| 5,554,118 A * | 9/1996 | Jang | A61M 25/0023 604/102.02 |
| 5,643,285 A | 7/1997 | Rowden et al. | |
| 5,840,077 A | 11/1998 | Rowden et al. | |
| 6,129,662 A | 10/2000 | Li et al. | |
| 6,423,075 B1 | 7/2002 | Singh et al. | |
| 6,516,216 B1 | 2/2003 | Fontenot et al. | |
| 6,582,401 B1 * | 6/2003 | Windheuser | A61M 25/00 604/164.05 |
| 8,025,670 B2 | 9/2011 | Sharp et al. | |
| 8,128,622 B2 | 3/2012 | Podhajsky et al. | |
| 8,192,444 B2 | 6/2012 | Dycus | |
| 8,206,357 B2 | 6/2012 | Bettuchi | |
| 8,292,901 B2 | 10/2012 | Auerbach et al. | |
| 8,298,213 B2 | 10/2012 | Singh | |
| 8,323,278 B2 | 12/2012 | Brecheen et al. | |
| 8,453,910 B2 | 6/2013 | Bettuchi et al. | |
| 8,460,289 B2 | 6/2013 | Sartor | |
| 8,528,563 B2 | 9/2013 | Gruber | |
| 8,545,513 B2 | 10/2013 | Blair et al. | |
| 8,603,105 B2 | 12/2013 | Sauer | |
| 8,663,239 B2 | 3/2014 | Hess | |
| 8,696,563 B2 | 4/2014 | Williams et al. | |
| 8,784,410 B2 | 7/2014 | Dunning | |
| 8,939,988 B2 | 1/2015 | Auerbach et al. | |
| 9,011,433 B2 | 4/2015 | Batchelor et al. | |
| 9,022,927 B2 | 5/2015 | Kleyman | |
| 9,033,977 B2 | 5/2015 | Morozov | |
| 9,066,724 B2 | 6/2015 | Jenkins | |
| 9,101,390 B2 | 8/2015 | Singh et al. | |
| 9,144,454 B2 | 9/2015 | Batchelor et al. | |
| 9,392,935 B2 | 7/2016 | Adams et al. | |
| 2003/0187334 A1 | 10/2003 | Biswas | |
| 2005/0085827 A1 | 4/2005 | G et al. | |
| 2005/0182387 A1 * | 8/2005 | Webler | A61M 25/0668 604/527 |
| 2006/0271037 A1 | 11/2006 | Maroney et al. | |
| 2006/0291195 A1 | 12/2006 | Horrell et al. | |
| 2008/0208210 A1 | 8/2008 | Blair et al. | |
| 2009/0143751 A1 * | 6/2009 | Loori | A61M 35/30 604/290 |
| 2010/0280524 A1 | 11/2010 | Lopez Zepeda | |
| 2011/0130769 A1 | 6/2011 | Boebel et al. | |
| 2011/0190689 A1 | 8/2011 | Bennett et al. | |
| 2012/0016185 A1 | 1/2012 | Sherts et al. | |
| 2012/0116416 A1 | 5/2012 | Neff et al. | |
| 2012/0143210 A1 | 6/2012 | Brecheen et al. | |
| 2012/0165826 A1 | 6/2012 | Rhemrev-Pieters | |
| 2012/0283718 A1 | 11/2012 | Cosmescu | |
| 2012/0323079 A1 | 12/2012 | Bakare et al. | |
| 2012/0330324 A1 | 12/2012 | Sauer | |
| 2013/0066328 A1 | 3/2013 | Singh et al. | |
| 2013/0085508 A1 | 4/2013 | Hess | |
| 2013/0110126 A1 | 5/2013 | Mujwid | |
| 2013/0131459 A1 | 5/2013 | Williams et al. | |
| 2014/0012305 A1 | 1/2014 | Horton et al. | |
| 2014/0303641 A1 | 10/2014 | Boebel et al. | |
| 2014/0358158 A1 | 12/2014 | Einarsson | |
| 2015/0005780 A1 | 1/2015 | Einarsson | |
| 2015/0080905 A1 | 3/2015 | Begemann et al. | |
| 2015/0127016 A1 | 5/2015 | Sauer | |
| 2015/0351621 A1 | 12/2015 | Hill et al. | |
| 2016/0045757 A1 | 2/2016 | Groseth | |
| 2016/0074186 A1 | 3/2016 | Sartor et al. | |
| 2016/0089039 A1 * | 3/2016 | Turturro | B32B 7/12 600/499 |
| 2016/0095649 A1 | 4/2016 | Motai et al. | |
| 2016/0100861 A1 | 4/2016 | Parys et al. | |
| 2016/0100862 A1 | 4/2016 | Parys | |
| 2016/0106463 A1 | 4/2016 | Egle et al. | |

FOREIGN PATENT DOCUMENTS

| | | |
|---|---|---|
| CN | 203244440 U | 10/2013 |
| CN | 203303125 U | 11/2013 |
| CN | 204446045 U | 7/2015 |
| CN | 204698659 U | 10/2015 |
| CN | 205072992 U | 3/2016 |
| DE | 102009018521 A1 | 10/2010 |
| EP | 0865760 A1 | 9/1998 |
| EP | 2243437 A1 | 10/2010 |
| WO | 03015643 A2 | 2/2003 |
| WO | 2008136024 A1 | 11/2008 |
| WO | 2011140604 A1 | 11/2011 |
| WO | 2012151622 A1 | 11/2012 |
| WO | 2013090909 A1 | 6/2013 |
| WO | 2016025132 A1 | 2/2016 |

* cited by examiner

OCCLUSION DEVICES, SYSTEMS, AND METHODS

CROSS REFERENCE TO RELATED APPLICATION

The present application claims the benefit of and priority to U.S. Provisional Application Ser. No. 62/545,703, filed on Aug. 15, 2017 the entire contents of which are incorporated herein by reference.

TECHNICAL FIELD

The present disclosure relates to surgical devices, systems, and methods and, more particularly, to occlusion devices, systems, and methods for maintaining pneumoperitoneum or another seal during a surgical procedure.

BACKGROUND

Sealing a surgical opening, e.g., a natural orifice or surgically-created opening, is often necessary in order to maintain pneumoperitoneum or for other purposes. During a laparoscopic hysterectomy, for example, the abdominal cavity is insufflated with a gas, or pneumoperitoneum, to distend and separate the abdominal wall from the uterus, such that the clinician can adequately view the surgical site and perform the hysterectomy. Laparoscopic hysterectomy is typically performed using a uterine manipulator including an occluder balloon that can be inflated within the vaginal cavity to prevent air from escaping and creating a loss of pneumoperitoneum. During the course of a laparoscopic hysterectomy, it may be necessary to introduce and withdraw the uterine manipulator multiple times, at least to create a seal to maintain pneumoperitoneum at various different points during the laparoscopic hysterectomy. Reintroducing the uterine manipulator into the vaginal cavity and re-inflating the occluder balloon multiple-times may be unnecessarily invasive.

SUMMARY

According to an aspect of the present disclosure, an occlusion device is provided, including a body having a plurality of layers and defining a first diameter. Each layer of the plurality of layers is releasably coupled to a respective inwardly-adjacent layer. An outermost layer of the plurality of layers is removable from the respective inwardly-adjacent layer. Removal of the outermost layer reduces an outer diameter of the body from the first diameter to a second diameter that is less than the first diameter.

In embodiments, the body further includes a central core, wherein an inner-most layer of the plurality of layers is disposed about the central core.

In some embodiments, the central core defines a lumen therethrough configured to receive a surgical instrument therein.

In certain embodiments, at least one layer of the plurality of layers includes a lubricious coating.

In embodiments, at least one layer of the plurality of layers is formed from a compressible material.

In some embodiments, the compressible material is a closed-cell foam.

In certain embodiments, each layer of the plurality of layers is releasably coupled to a respective inwardly-adjacent layer via a release feature selected from the group consisting of: hook and loop fasteners, glue, and tape.

In embodiments, the body defines a circular cross-sectional shape.

In some embodiments, application of a tensile force to the outermost layer removes the outermost layer from the inwardly-adjacent layer.

According to another aspect of the present disclosure, a uterine manipulator is provided, including a handle, a shaft extending distally from the handle, an end effector assembly disposed at a distal end portion of the shaft, and an occlusion device supported on the shaft. The occlusion device includes a body including a plurality of layers and defining a first diameter. Each layer of the plurality of layers is releasably coupled to a respective inwardly-adjacent layer. An outermost layer of the plurality of layers is removable from the respective inwardly-adjacent layer. Removal of the outermost layer reduces an outer diameter of the body from the first diameter to a second diameter that is less than the first diameter.

In embodiments, the body further includes a central core, wherein an inner-most layer of the plurality of layers is disposed about the central core.

In some embodiments, at least one layer of the plurality of layers includes a lubricious coating.

In certain embodiments, at least one layer of the plurality of layers is formed from a compressible material.

In embodiments, the compressible material is a closed-cell foam.

In some embodiments, the body defines a circular cross-sectional shape.

In certain embodiments, application of a tensile force to the outermost layer removes the outermost layer from the inwardly-adjacent layer.

According to yet another aspect of the present disclosure, a method for performing a surgical procedure is provided, including, determining the size of a body cavity, providing an occlusion device having a plurality of layers and defining a first diameter, applying a tensile force to a first outermost layer of the plurality of layers to remove the first outermost layer from the occlusion device such that an outer diameter of the occlusion device is reduced from the first diameter to a second diameter less than the first diameter, and positioning the occlusion device within the body cavity and forming a seal therein.

In embodiments, the method includes insufflating a surgical site with a gas to create a pneumoperitoneum therein.

In some embodiments, the method includes applying a tensile force to a second outermost layer of the plurality of layers to remove the second outermost layer from the occlusion device such that the outer diameter of the occlusion device is further reduced from the second diameter to a third diameter less than the second diameter.

BRIEF DESCRIPTION OF THE DRAWINGS

Objects and features of the present disclosure will become apparent to those of ordinary skill in the art when descriptions thereof are read with reference to the accompanying drawings, of which.

DETAILED DESCRIPTION

Figure 2A:
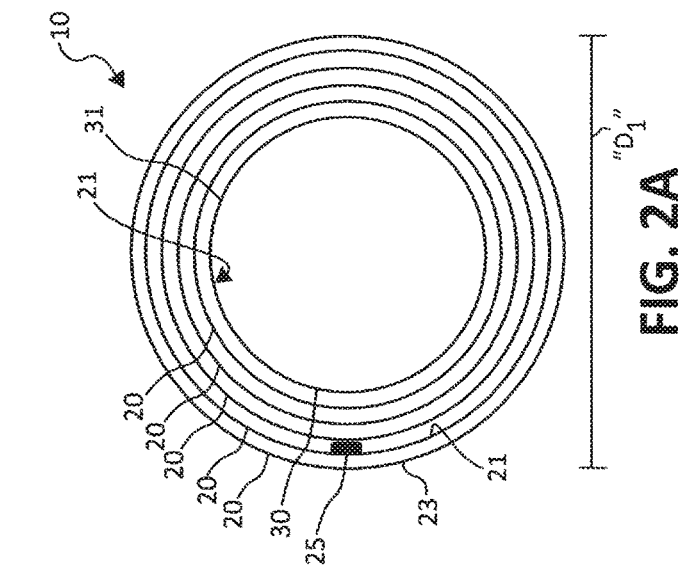
FIG. 2A is a cross-sectional view of the occlusion device of FIG. 1 taken along section line A-A of FIG. 1.
Figure 2C:
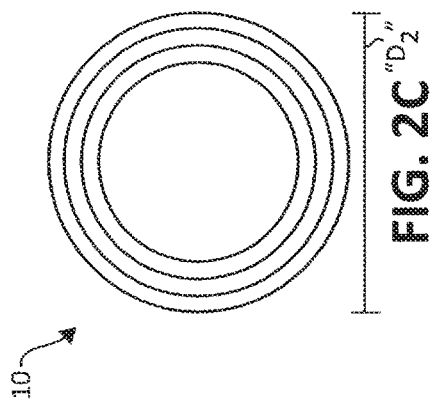
FIG. 2C is a cross-sectional view of the occlusion device of FIG. 1 with the outer-most layer of FIG. 2B removed.
Figure 1:
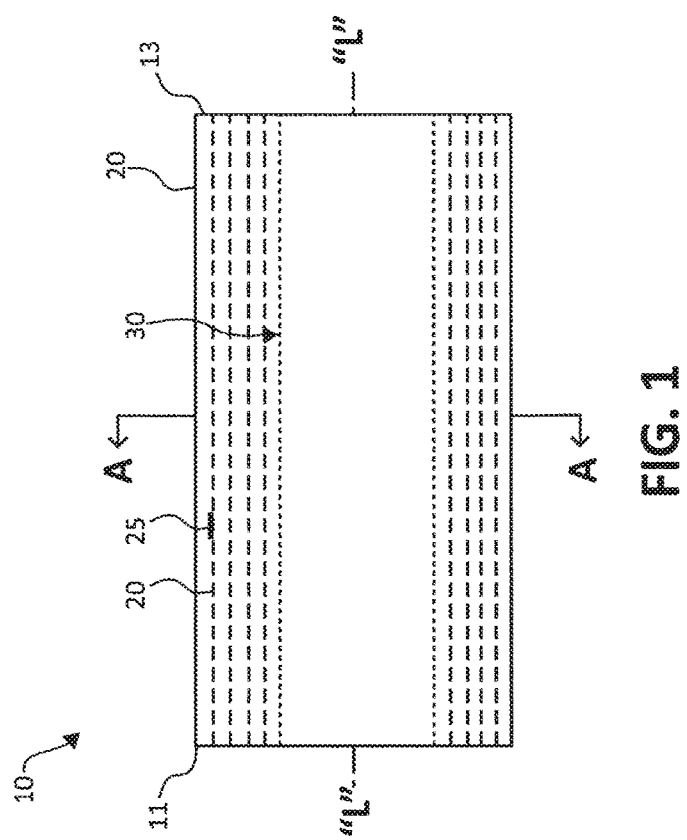
FIG. 1 is a side view of an occlusion device in accordance with the present disclosure.
Figure 2B:
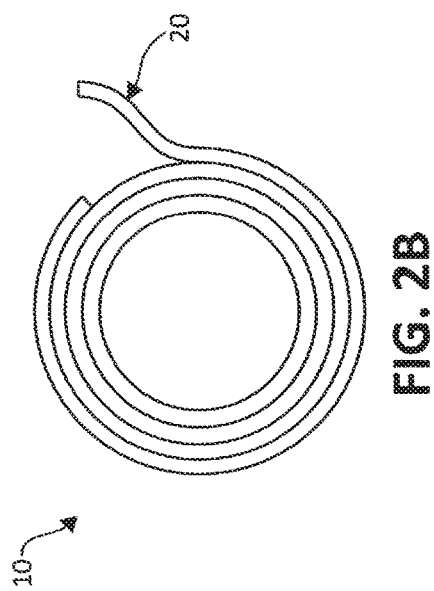
FIG. 2B is a cross-sectional view of the occlusion device of FIG. 1 illustrating partial removal of an outer-most layer.

Embodiments of the present disclosure are described in detail with reference to the drawings in which like reference numerals designate identical or corresponding elements in each of the several views. As used herein, the term "distal" refers to that portion of structure farther from the user, while the term "proximal" refers to that portion of structure closer to the user. As used herein, the term "clinician" refers to a doctor, nurse, or other care provider and may include support personnel. In the following description, well-known functions or constructions are not described in detail to avoid obscuring the present disclosure in unnecessary detail.

Referring to FIGS. 1 and 2A-2C, an occlusion device is shown generally identified by reference numeral 10. Occlusion device 10 is configured for slidable positioning within an artificial or natural opening of a patient (e.g., a body orifice) to maintain pneumoperitoneum or another seal therein. Occlusion device 10 generally defines a longitudinal axis "L-L" and includes a first end portion 11, a second end portion 13, and a plurality of layers of material 20 with each layer 20 (except for the inner-most layer 20) surrounding an inwardly adjacent layer 20.

Each layer 20 is disposed in surrounding relation about, releasably coupled to, and removable from, each inwardly adjacent layer 20 (with the exception of the inner-most layer 20 for which there is no inwardly adjacent layer). For example, an outermost layer 20 is removable from an inwardly-adjacent layer 20, similar to peeling away layers of an onion, as described below. Each layer 20 defines an inner surface 21 and an outer surface 23. Each layer 20 increases the outer diameter of occlusion device 10. For example, with the outermost layer 20 disposed on occlusion device 10, occlusion device 10 has an outer diameter "$D_1$" (FIG. 2A), while, with the outermost layer 20 removed (FIG. 2B), a layer 20 inwardly adjacent to the outermost layer 20 defines an outer diameter "$D_2$" (FIG. 2C) of the occlusion device 10 that is less than diameter "$D_1$."

Some or all of the layers 20 may be color-coded to indicate to the clinician the diameter of the occlusion device at each layer 20. Likewise, some or all of the layers 20 may include other indicia or markings to indicate to the surgeon the diameter of the occlusion device at each layer 20.

Some or all of the layers 20 may be formed from or include any suitable resiliently deformable material. For example, some or all of the layers 20 may be formed from a closed cell foam material, such as polyisoprene, polyethylene, cross-linked polyethylene, polypropylene, neoprene, polystyrene, etc. Some or all of the layers 20 may be a "memory" foam having sufficient compliance to form a seal about a body orifice (e.g., the vaginal cavity) upon insertion into the body orifice to conform therewith. It is contemplated that one or more of the layers 20 may be formed from a different material or may have different properties, e.g., thickness, density, etc., from one or more other layers 20, such that occlusion device 10 defines a composite structure.

A lubricious biocompatible coating, such as parylene N or C, may be applied to some or all of the layers 20 in order to ensure that such layers 20 does not unnecessarily cause friction against a body orifice without diminishing the ability to establish a fluid-tight seal therewith. The lubricious coating may also be configured to, e.g., facilitate removal of such layers 20 from a respective inwardly-adjacent layer 20. Although each layer 20 is shown as having a cylindrical shape, each layer 20 may have any suitable shape, such as rectangular, square, triangular, elliptical, trapezoidal, or the like, to sufficiently seal a body orifice, for example, to maintain pneumoperitoneum therein. Additionally or alternatively, each layer 20 may define a cup-like shape or configuration. For example, each layer 20 may be open at a first end thereof, and closed at a second end thereof.

At least one of inner and outer surfaces 21, 23 of some or all of the layers 20 may include a retention feature (not explicitly shown) to releasably couple each of such layers 20 to an adjacent layer 20. The retention feature may be a biocompatible adhesive (e.g., glue), hook and loop fasteners (e.g., Velcro®), tape, or other suitable retention feature.

At least one of inner and outer surfaces 21, 23 of some or all of the layers 20 may include a release feature 25. Release feature 25 may include a plurality of perforations extending through respective inner and outer surfaces 21, 23 of each layer 20. Release feature 25 may alternatively or additionally include a peel tape, a shrink tape, a tear tape, or the like. When a sufficient tensile force is applied to, e.g., an outermost layer or layers 20, the outermost layer 20 disengages or separates from an inwardly adjacent layer 20 such that the outermost layer 20 may be completely removed from the occlusion device 10, as will be described below. Release feature 25 may be part of the retention feature, e.g., as in embodiments where hook and loop fasteners are utilized, or may be separate therefrom, e.g., wherein the retention feature is an adhesive.

Continuing with reference to FIGS. 1 and 2A-2C occlusion device 10 may include a central core 30. Central core 30 may define a shape of occlusion device 10 and/or may provide structural rigidity to occlusion device 10. Central core 30 includes an outer surface 31 that is in contact with inner surface 21 of an innermost layer 20. Central core 30 may be disposed between respective first and second end portions 11, 13 of occlusion device 10.

Central core 30 may be formed from any suitable material including rigid, semi-rigid, or pliable materials. For example, central core 30 may be formed from a closed cell foam material, such as polyisoprene, polyethylene, cross-linked polyethylene, polypropylene, neoprene, polystyrene, etc. Central core 30 may be a "memory" foam having sufficient compliance to form a seal about a body orifice (e.g., the vaginal cavity) upon insertion into the body orifice to conform therewith. A lubricious biocompatible coating, such as parylene N or C, may be applied to the outer surface 31 of central core 30, e.g., to facilitate removal of an innermost layer 20 from central core 30. Although central core 30 is shown as having a cylindrical shape, central core 30 may have any suitable shape, such as rectangular, square, triangular, elliptical, trapezoidal, or the like, to sufficiently seal a body orifice and to maintain pneumoperitoneum therein. Central core 30 may define a lumen therethrough (not explicitly shown) such that occlusion device 200 is configured to receive a surgical instrument therethrough.

It is contemplated that occlusion device 10 may be used, with, or without central core 30. For example, occlusion device 10 may be made entirely of layers 20. Additionally, central core 30 may be used as a standalone device (e.g., once all layers 20 have been removed) to maintain pneumoperitoneum within a body cavity and/or for other purposes, e.g., as an access device.

Figure 3:
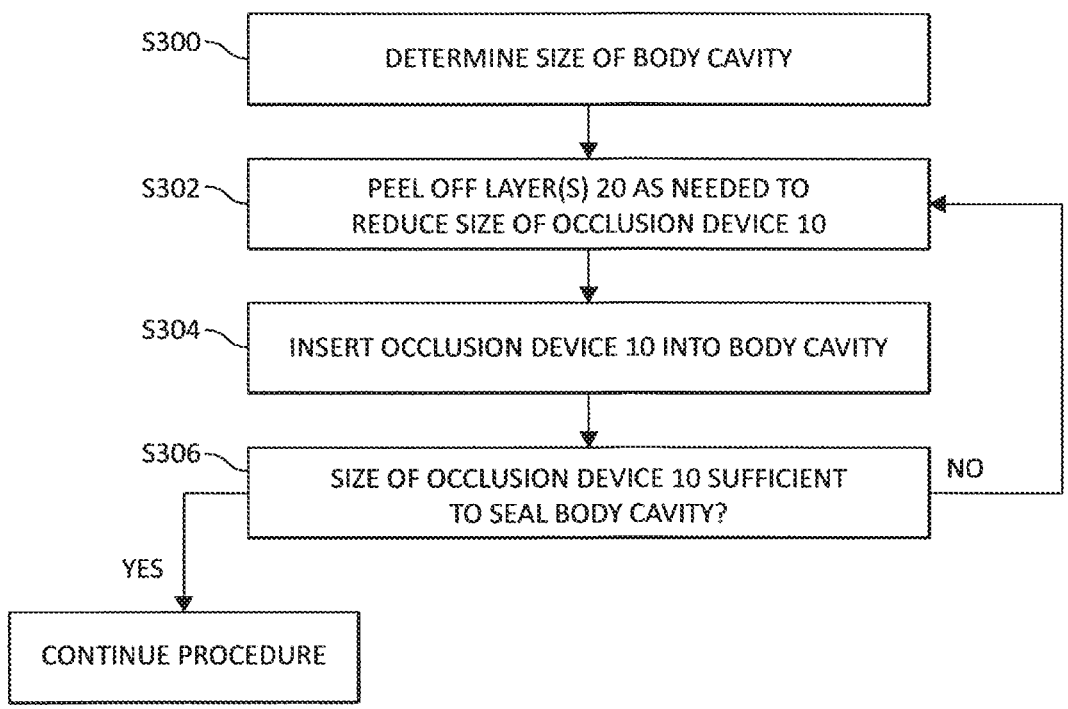
FIG. 3 is a flowchart illustrating a method of a performing a surgical procedure in accordance with the present disclosure.

Referring now to FIG. 3, a method in accordance with the present disclosure is described. The method of FIG. 3, although necessarily illustrated and described in an order, is not intended to have any limiting effect or to imply any particular order. To this end, the methods illustrated and described herein may include some or all of the features described and may be implemented in any suitable order.

Figure 4:
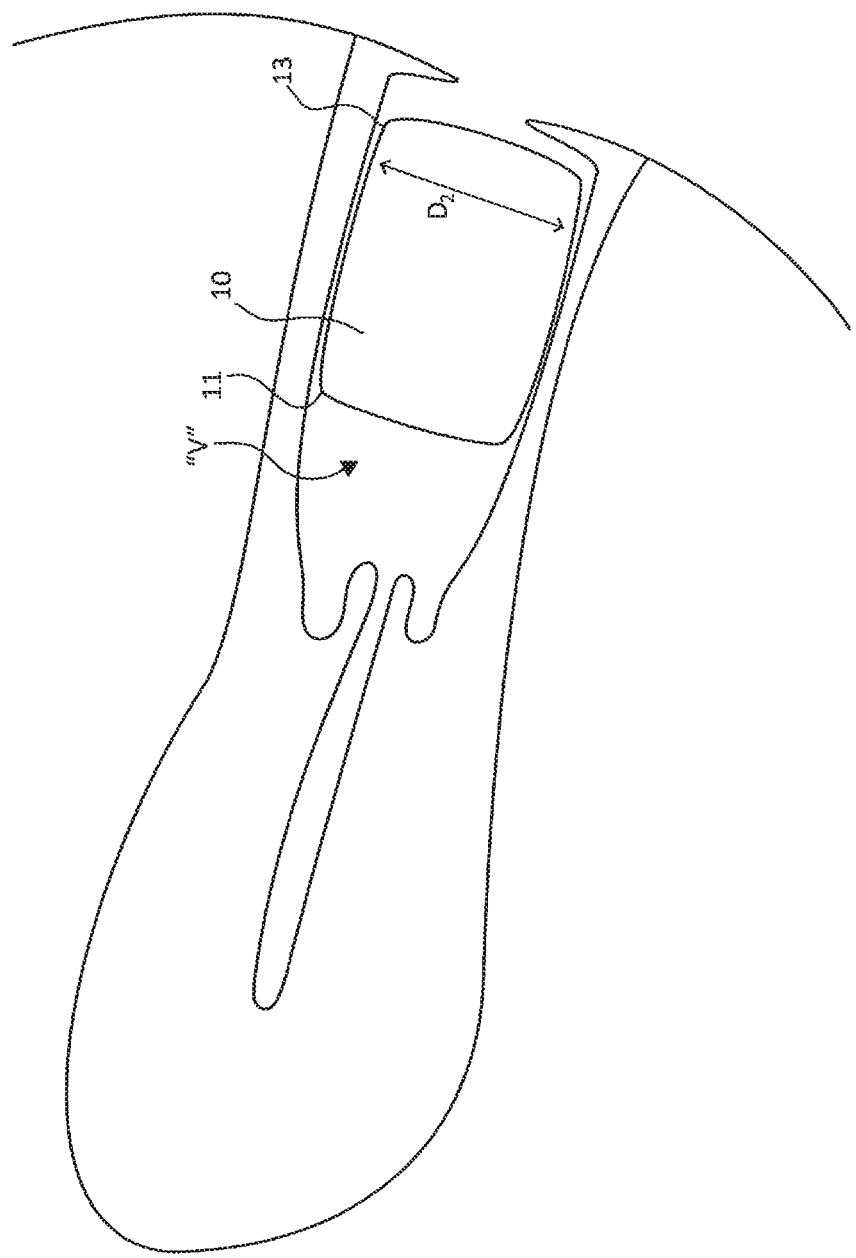
FIG. 4 is a schematic diagram of the occlusion device of FIG. 1, disposed within a vaginal cavity.

With reference to FIGS. 3 and 4, in use, during for example, a laparoscopic hysterectomy, the abdominal cavity is insufflated with a gas, or pneumoperitoneum, to distend and separate the abdominal wall from the uterus, such that the clinician can adequately view the surgical site and perform, e.g., a colpotomy procedure. In 5300, a clinician determines the size of the body cavity, e.g., vaginal cavity "V." In 5302, as many layers 20 may be peeled away from occlusion device 10 as necessary to reduce the size of occlusion device 10 to match the size of the vaginal cavity "V." Specifically, a tensile force is applied to outermost layer or layers 20 of occlusion device 10 to cause release feature 25 of the outermost layer(s) 20 to decoupled the outermost layer or layers 20 from the inwardly-adjacent layer 20 such that outermost layer(s) 20 is removed from occlusion device 10. Where multiple layers 20 are to be removed, such may be removed individually one layer 20 at a time or multiple layers 20 at a time. With occlusion device 10 thus having an appropriate size according to the determined size of the vagina cavity "V" (e.g., for atraumatic insertion of occlusion device 10 in vaginal cavity "V" and for maintaining pneumoperitoneum in vaginal cavity "V"), in 5304, occlusion device 10 is inserted into vaginal cavity "V" to a desired depth. In 5306, if the size of occlusion device 10 is appropriate, then the clinician may continue the procedure.

If the size of occlusion device 10 is not appropriate (e.g., too large), then the clinician, in 5306, may withdraw occlusion device 10 from the vaginal cavity "V" and remove as many layers 20 from occlusion device 10 as necessary to reduce the size of occlusion device 10 (e.g., from diameter "$D_1$" to diameter "$D_2$", FIG. 2) such that occlusion device 10 is of appropriate size. Alternatively, if occlusion device 10 is deemed to be too small, layers 20 may be added back onto occlusion device 10. The clinician may then atraumatically re-insert occlusion device 10 into the vaginal cavity "V" such that insufflation gases used during the procedure to enlarge the area surrounding the surgical site do not escape through the vaginal cavity "V" and out of the patient. In this way, pneumoperitoneum is maintained and the clinician can continue or complete, e.g., the hysterectomy procedure. Upon completion of the procedure, occlusion device 10 may be removed (e.g., using surgical forceps, by hand, etc.).

Figure 5:
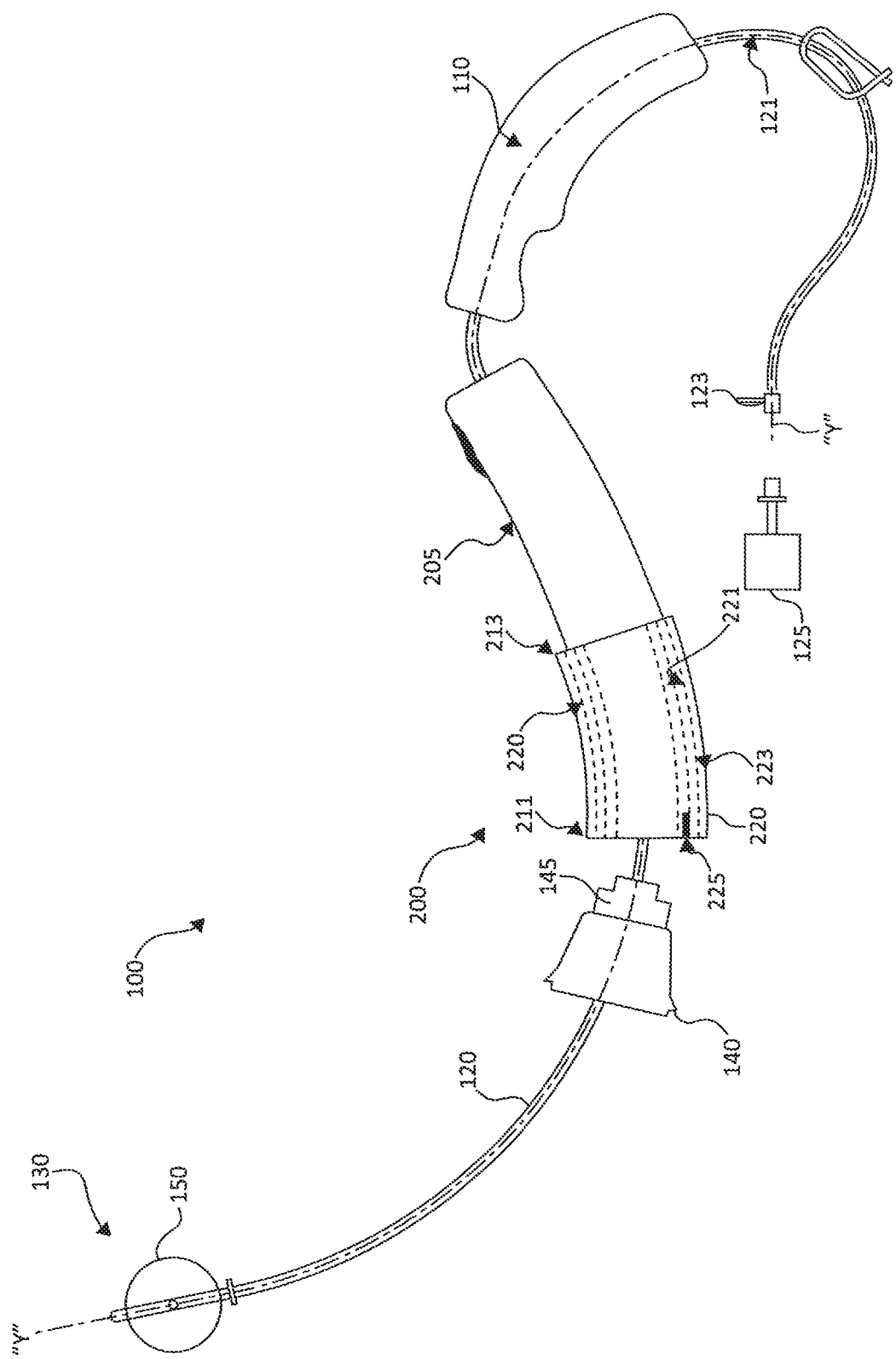
FIG. 5 is a side view of a uterine manipulator including an occlusion device in accordance with the present disclosure.

With reference to FIG. 5, in accordance with another embodiment of the present disclosure, a uterine manipulator is shown and generally identified by reference numeral 100. Uterine manipulator 100 is generally adapted for insertion through the vaginal cavity "V" and into the uterus "U" and is used to mobilize and/or position the uterus "U" during pelvic surgical procedures, e.g., laparoscopic hysterectomy. Uterine manipulator 100 defines a central axis "Y-Y" and generally includes a handle 110, a shaft 120 extending from handle 110, an occlusion device 200 supported on a slidable occluder shaft 205, a uterine manipulating tip portion 130, a cervical cup 140, a shuttle 145, and an inflatable balloon 150.

Handle 110 of uterine manipulator 100 is configured for gripping and/or using uterine manipulator 100. Movement (e.g., pivoting, rotation, etc.) of handle 110 causes uterine manipulating tip portion 130 to move about central axis "Y-Y" for moving and/or positioning the uterus "U," for example, for retroversion and anteversion of the uterus.

Shaft 120 extends distally from handle 110 and is generally an elongated tube configured for insertion through the vaginal cavity "V" and into the uterus "U." Shaft 120 includes an actuation assembly (not shown) disposed therein, which is operatively connected to handle 110 at a proximal end portion thereof to enable manipulation of the uterus "U." Shaft 120 includes a fluid conduit 121 disposed therein that is connected to port 123 at a proximal end portion thereof and to inflatable balloon 150 at a distal end portion thereof. Port 123 couples to an inflation source 125 for delivering inflation fluid (e.g., saline, air, or the like) from inflation source 125 through fluid conduit 121 to inflatable balloon 150, such that inflatable balloon 150 may be inflated with the inflation fluid.

Occlusion device 200 is similar to occlusion device 10 described above, except that occlusion device 200 is configured for use with uterine manipulator 100. Specifically, layers 220 of occlusion device 200 are wrapped around shaft 205 of uterine manipulator 100 in sealing engagement thereabout.

Occlusion device 200 may additionally include a central core 230 that is in sealing engagement with shaft 205 of uterine manipulator 100. Specifically, in embodiments including central core 230, central core 230 defines a lumen therethrough configured to receive shaft 205 of uterine manipulator 100.

Occlusion device 200 generally defines a longitudinal axis "L" and includes a first end portion 211, a second end portion 213 and a plurality of layers of material 220 with each layer 220 (except for the inner-most layer 20) surrounding an inwardly adjacent layer 220. Each layer 220 is disposed in surrounding relation about, releasably coupled to, and removable from, each inwardly adjacent layer 220 (with the exception of the inner-most layer 220 for which there is no inwardly adjacent layer). For example, an outermost layer 220 is removable from an inwardly-adjacent layer 220, similar to peeling away layers of an onion, as described above with respect to occlusion device 10. Each layer 220 defines an inner surface 221 and an outer surface 223. Each layer 220 increases the outer diameter of occlusion device 200. For example, with the outermost layer 220 disposed on occlusion device 200, occlusion device 200 has an outer diameter "$D_1$," while, with the outermost layer 220 removed, a layer 220 inwardly adjacent to the outermost layer 220 defines an outer diameter "$D_2$" of the occlusion device 10 that is less than diameter "$D_1$."

At least one of inner and outer surfaces 221, 223 of some or all of the layers 220 may include a retention feature (not explicitly shown) to releasably couple each of such layers 220 to an adjacent layer 220. The retention feature may be a biocompatible adhesive (e.g., glue), hook and loop fasteners (e.g., Velcro®), tape, or other suitable retention feature. At least one of inner and outer surfaces 221, 223 of some or all of the layers 220 may include a release feature 225. Release feature 225 may include a plurality of perforations extending through respective inner and outer surfaces 221, 223 of each layer 220. Release feature 225 may alternatively or additionally include a peel tape, a shrink tape, a tear tape, or the like. When a sufficient tensile force is applied to, e.g., an outermost layer or layers 220, the outermost layer 220 disengages or separates from an inwardly adjacent layer 220 such that the outermost layer 220 may be completely removed from the occlusion device 200. Release feature 225 may be part of the retention feature, e.g., as in embodiments where hook and loop fasteners are utilized, or may be separate therefrom, e.g., wherein the retention feature is an adhesive.

Occlusion device 200 may be formed separately from, or integrally with uterine manipulator 100. Occlusion device 200 may be attached to any surface of uterine manipulator 100, such as any portion of slidable occluder shaft 205, shaft 120, or the like. Occlusion device 200 may be rigidly attached to any surface of uterine manipulator 100 (e.g., via adhesives, fasteners, etc.). Alternatively, occlusion device 200 may be slidably and/or frictionally engaged with any surface of uterine manipulator 100, such that occlusion device 200 may be moved proximally or distally along uterine manipulator 100, or separated from uterine manipulator 100 as needed. For example, occlusion device 200 may be attached to slidable occluder shaft 205, which is movable proximally and/or distally along shaft 120.

Although occlusion device 200 is described herein for use with uterine manipulator 100, occlusion device 200 may be adapted for use with any suitable surgical instrument. The surgical instrument may, for example, be an access instrument configured to receive additional instrumentation therethrough, may itself be configured to perform one or more surgical tasks, and/or may be configured to facilitate insertion and/or removal of occlusion device 200.

Uterine manipulating tip portion 130 is configured for insertion into the uterus "U" and includes cervical cup 140 disposed on a proximal portion thereof and inflatable balloon 150 disposed at a distal end portion thereof. Cervical cup 140 generally defines a cup-like configuration configured to abut and envelope the cervix, e.g., for displacing the cervix away from the uterus, retracting the bladder, and/or defining cervical points of reference for a colpotomy incision. Shuttle 145 may be selectively coupled to cervical cup 140 to enable cervical cup 140 and shuttle 145 to move together. A distal end portion of uterine manipulating tip portion 130 includes inflatable balloon 150, which is configured to selectively inflate with inflation fluid from inflation source 125 for anchoring the uterine manipulator 100 within the uterus "U."

Figure 6:
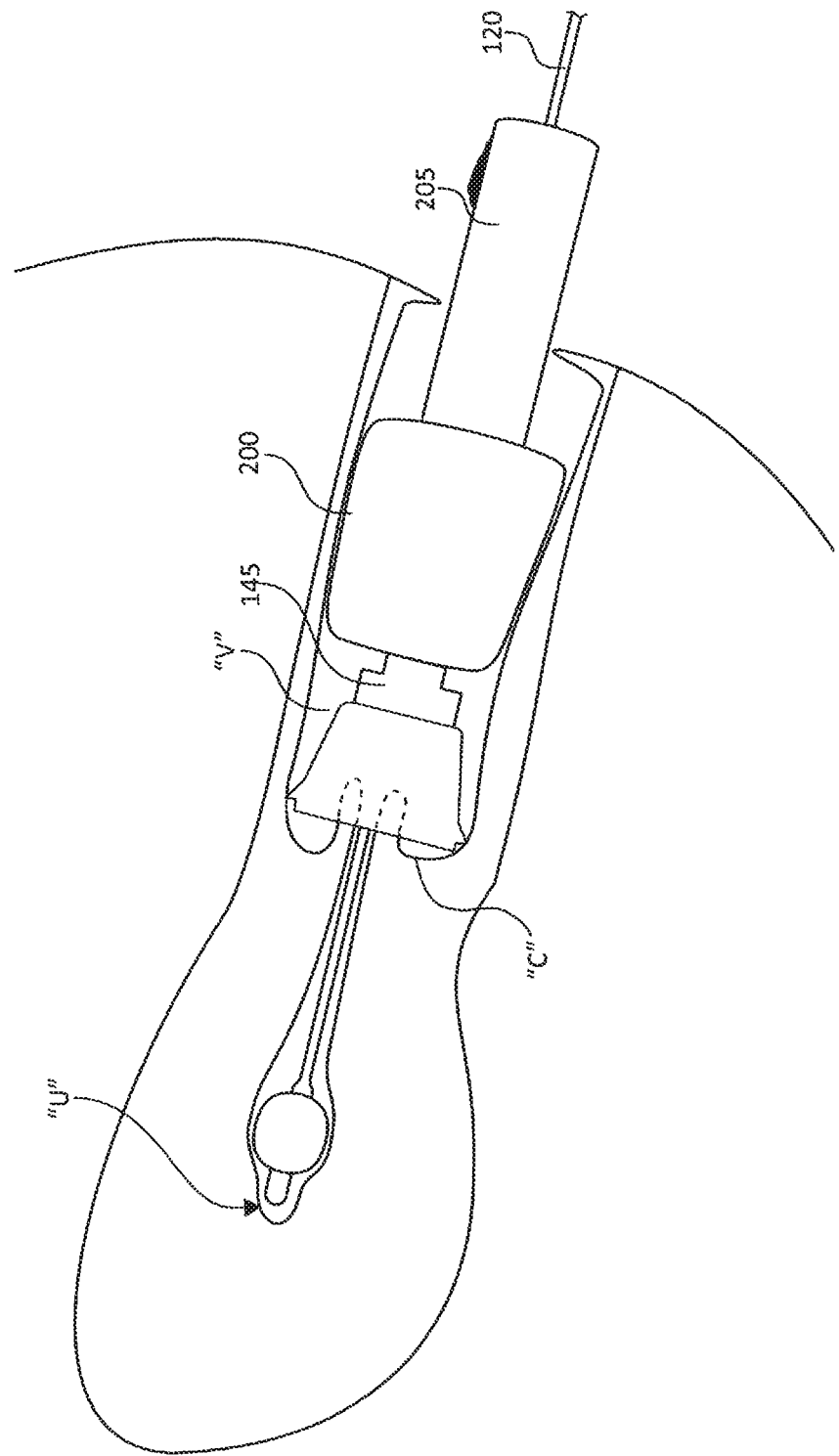
FIG. 6 is a schematic diagram of a distal end portion of the uterine manipulator of FIG. 5 disposed within the vaginal cavity.

In use, during for example, a laparoscopic hysterectomy, the abdominal cavity is insufflated with a gas, or pneumoperitoneum, to distend and separate the abdominal wall from the uterus, such that the clinician can adequately view the surgical site and perform, e.g., a colpotomy procedure. With reference to FIG. 6, uterine manipulating tip portion 130 of uterine manipulator 100 is advanced distally through the vaginal cavity "V" of a patient until the cervical cup 140 is in abutment with the cervix "C" and the uterine manipulating tip portion 130 is placed within the uterus "U."

Once the clinician determines the size of the vaginal cavity "V, as many layers 220 may be peeled away from occlusion device 200 as necessary to reduce the size of occlusion device 200 (e.g., from diameter "$D_1$" to diameter "$D_2$" (FIG. 2)) to conform to vaginal cavity "V."

Port 123 is coupled to inflation source 125 for delivering inflation fluid from port 123 through fluid conduit 121 to inflatable balloon 150 to inflate inflatable balloon 150. With inflatable balloon 150 of uterine manipulating tip portion 130 inflated, uterine manipulator 100 is anchored to the uterus "U" such that the uterus "U" can be positioned, e.g., for the colpotomy incision.

Movement of handle 110 causes movement of uterine manipulating tip portion 130, which causes movement of the uterus "U." Specifically, movement of handle 110 causes movement of uterine manipulating tip portion 130 about central axis "Y-Y" for retroversion and anteversion of the uterus.

As shown in FIG. 6, an appropriately sized occlusion device 200 substantially conforms to, and seals the vaginal cavity "V" such that the insufflation gases used during the procedure to enlarge the area surrounding the hysterectomy target site, or pneumoperitoneum, do not escape through the vaginal cavity "V." A clinician may then create a colpotomy incision (not shown) to, e.g., separate part or all of the uterus from the vagina. With the colpotomy created and the uterus separated from the vagina, the clinician may withdraw uterine manipulator 100 from the vaginal cavity "V" with the severed uterus attached to uterine manipulating tip portion 130.

With uterine manipulator 100 removed from the vaginal cavity "V," pneumoperitoneum must still be maintained in order for the clinician to maintain the surgical field of view during laparoscopy such that the clinician can seal off the vaginal cuff to complete the procedure. As can be appreciated, re-inserting a uterine manipulator into the vaginal cavity "V" in order to maintain pneumoperitoneum may increase the risk of inadvertent trauma to the patient's cervix "C," intact sections of the uterus "U" (if any), or other tissue. Rather than re-inserting uterine manipulator 100 into the vaginal cavity "V" to maintain pneumoperitoneum, the clinician may instead insert occlusion device 10 into the vaginal cavity "V," as detailed above with respect to FIGS. 3 and 4. In this way, pneumoperitoneum is maintained quickly and effectively with minimal invasiveness to the patient. The clinician can then laparoscopically seal off the vaginal cuff to complete the hysterectomy. Once completed, the clinician can remove occlusion device 10 from the vaginal cavity "V."

It should be appreciated that devices, systems, and methods described herein may be used for any type of surgical procedure and are not limited to laparoscopic hysterectomy procedures.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An occlusion device, comprising:
   a body including a plurality of layers and defining a first diameter, each layer of the plurality of layers releasably coupled to a respective inwardly-adjacent layer,
   wherein at least one layer of the plurality of layers includes a lubricious coating, wherein an outermost layer of the plurality of layers is removable from the respective inwardly-adjacent layer, wherein removal of the outermost layer reduces an outer diameter of the body from the first diameter to a second diameter that is less than the first diameter, and wherein the outermost layer of the plurality of layers is releasably coupled to the respective inwardly-adjacent layer via a hook and loop fastener release feature.

2. The occlusion device according to claim 1, wherein the body further includes a central core, wherein an inner-most layer of the plurality of layers is disposed about the central core.

3. The occlusion device according to claim 2, wherein the central core defines a lumen therethrough configured to receive a surgical instrument therein.

4. The occlusion device according to claim 1, wherein at least one layer of the plurality of layers is formed from a compressible material.

5. The occlusion device according to claim 4, wherein the compressible material is a closed-cell foam.

6. The occlusion device according to claim 1, wherein the body defines a circular cross-sectional shape.

7. The occlusion device according to claim 1, wherein application of a tensile force to the outermost layer removes the outermost layer from the inwardly-adjacent layer.

8. The occlusion device according to claim 1, wherein each layer of the plurality of layers defines a shape selected from the group consisting of rectangular, square, triangular, elliptical, and trapezoidal.

9. The occlusion device according to claim 1, wherein at least one layer of the plurality of layers further includes a plurality of perforations extending through an inner surface and an outer surface thereof.

10. A uterine manipulator, comprising:
a handle;
a shaft extending distally from the handle;
an end effector assembly disposed at a distal end portion of the shaft;
an occlusion device supported on the shaft, including:
a body including a plurality of layers and defining a first diameter, each layer of the plurality of layers releasably coupled to a respective inwardly-adjacent layer,
wherein at least one layer of the plurality of layers includes a lubricious coating, wherein an outermost layer of the plurality of layers is removable from the respective inwardly-adjacent layer, wherein removal of the outermost layer reduces an outer diameter of the body from the first diameter to a second diameter that is less than the first diameter, and wherein the outermost layer of the plurality of layers is releasably coupled to the respective inwardly-adjacent layer via a hook and loop fastener release feature.

11. The uterine manipulator according to claim 10, wherein the body further includes a central core, wherein an inner-most layer of the plurality of layers is disposed about the central core.

12. The uterine manipulator according to claim 10, wherein at least one layer of the plurality of layers includes a lubricious coating.

13. The uterine manipulator according to claim 10, wherein at least one layer of the plurality of layers is formed from a compressible material.

14. The uterine manipulator according to claim 13, wherein the compressible material is a closed-cell foam.

15. The occlusion device according to claim 10, wherein the body defines a circular cross-sectional shape.

16. The uterine manipulator according to claim 10, wherein application of a tensile force to the outermost layer removes the outermost layer from the inwardly-adjacent layer.

17. The uterine manipulator according to claim 10, wherein each layer of the plurality of layers defines a shape selected from the group consisting of rectangular, square, triangular, elliptical, and trapezoidal.

18. An occlusion device, comprising:
a body including a plurality of layers and defining a first diameter, each layer of the plurality of layers releasably coupled to a respective inwardly-adjacent layer,
wherein an outermost layer of the plurality of layers is removable from the respective inwardly-adjacent layer, and wherein removal of the outermost layer reduces an outer diameter of the body from the first diameter to a second diameter that is less than the first diameter, the outermost layer of the plurality of layers releasably coupled to the respective inwardly-adjacent layer via a hook and loop fastener release feature, and
wherein at least one layer of the plurality of layers further includes a plurality of perforations extending through an inner surface and an outer surfaces thereof.

19. The occlusion device according to claim 18, wherein the body further includes a central core, wherein an inner-most layer of the plurality of layers is disposed about the central core.

20. The occlusion device according to claim 19, wherein the central core defines a lumen therethrough configured to receive a surgical instrument therein.

* * * * *